United States Patent
Gupta et al.

(10) Patent No.: US 12,347,562 B2
(45) Date of Patent: Jul. 1, 2025

(54) DECISION SUPPORT APPLICATION FOR PCOS

(71) Applicant: CERNER INNOVATION, INC., Kansas City, KS (US)

(72) Inventors: Deepak Gupta, Bangalore (IN); Kavya Gupta, Bangalore (IN); Nikhila A, Kerala (IN); Nitha Thammaiah, Bangalore (IN)

(73) Assignee: Cerner Innovation, Inc., Kansas City, MO (US)

( * ) Notice: Subject to any disclaimer, the term of this patent is extended or adjusted under 35 U.S.C. 154(b) by 93 days.

(21) Appl. No.: 16/727,185

(22) Filed: Dec. 26, 2019

(65) Prior Publication Data

US 2021/0202095 A1 Jul. 1, 2021

(51) Int. Cl.
| | | |
|---|---|---|
| *G16H 50/30* | (2018.01) | |
| *G16H 10/60* | (2018.01) | |
| *G16H 40/60* | (2018.01) | |
| *G16H 50/20* | (2018.01) | |
| *G16H 50/70* | (2018.01) | |

(52) U.S. Cl.
CPC ............ *G16H 50/30* (2018.01); *G16H 10/60* (2018.01); *G16H 40/60* (2018.01); *G16H 50/20* (2018.01); *G16H 50/70* (2018.01)

(58) Field of Classification Search
CPC ........ G16H 50/30; G16H 50/20; G16H 40/60; G16H 10/60; G16H 50/70; G06F 16/24578; G06F 19/30; G06F 19/32; G06F 19/34; G06F 19/36; G06Q 50/22; G06Q 50/02
See application file for complete search history.

(56) References Cited

U.S. PATENT DOCUMENTS

| | | | |
|---|---|---|---|
| 10,483,003 B1* | 11/2019 | McNair | G16H 10/60 |
| 2016/0220302 A1* | 8/2016 | Zarins | A61B 8/0841 |
| 2017/0333126 A1* | 11/2017 | Sobotka | A61B 18/1482 |
| 2019/0080031 A1* | 3/2019 | Herman | G06Q 40/08 |
| 2019/0374193 A1* | 12/2019 | Ramachandran | A61B 8/0858 |
| 2020/0043612 A1* | 2/2020 | McNair | G16H 10/60 |

(Continued)

FOREIGN PATENT DOCUMENTS

| | | | | |
|---|---|---|---|---|
| CN | 105023220 A | * | 8/2015 | G06Q 50/22 |
| JP | 2017212042 A | * | 11/2017 | |

(Continued)

OTHER PUBLICATIONS

Soni, et. al., Exploration on Polycystic Ovarian Syndrome and Data Mining Techniques, Oct. 1, 2018 (Year: 2018).*

(Continued)

*Primary Examiner* — David J Stoltenberg
(74) *Attorney, Agent, or Firm* — Invoke

(57) ABSTRACT

Aspects of the present disclosure determine a risk level of Polycystic Ovarian syndrome ("PCOS"). Alongside the risk level of PCOS, aspects of the present disclosure simultaneously display the risk level of PCOS with patient information, which may be useful for clinicians. Aspects include receiving patient information of a patient, determining a patient criteria is satisfied based on the patient information, and applying a predictive diagnosis model to the patient information to determine a risk level of PCOS.

37 Claims, 9 Drawing Sheets

(56) References Cited

U.S. PATENT DOCUMENTS

2020/0281945 A1* 9/2020 Sharp .................... A61K 47/14

FOREIGN PATENT DOCUMENTS

| WO | WO-2015197858 A1 * | 12/2015 | ........... C12Q 1/6883 |
| WO | WO-2018210646 A1 * | 11/2018 | ............. G06N 20/00 |

OTHER PUBLICATIONS

Williams, et. al., Diagnosis and Treatment of Polycystic Ovary Syndrome, Jul. 15, 2016 (Year: 2016).*

Denny et al., i-HOPE: Detection and Prediction System for Polycystic Ovary Syndrome (PCOS) Using Machine Learning Techniques, 978-1-7281-1895-6/19/$31.00_c 2019 IEEE.*

Azziz, Ricardo, "Diagnosis of Polycystic Ovarian Syndrome: The Rotterdam Criteria Are Premature", The Journal of Clinical Endocrinology & Metabolism, vol. 91, Issue 3, Mar. 1, 2006, pp. 781-785.

Barthelmess et al., "Polycystic Ovary Syndrome: Current Status and Future Perspective", Frontiers in Bioscience (Elite Ed.), vol. 6, Jan. 1, 2014, pp. 104-119.

Bharathi et al., "An Epidemiological Survey: Effect of Predisposing Factors for PCOS in Indian Urban and Rural Population", Middle East Fertility Society Journal, vol. 22, Issue 4, Dec. 2017, pp. 313-316.

Bozdag et al., "The Worldwide Prevalence and Phenotypic Features of Polycystic Ovary Syndrome", Atlas of Science, Available online at: <https://atlasofscience.org/the-worldwide-prevalence-and-phenotypic-features-of-polycystic-ovary-syndrome/>, Jun. 27, 2017, pp. 1-3.

Broekmans et al., "PCOS according to the Rotterdam Consensus Criteria: Change in Prevalence among WHO-II Anovulation and Association with Metabolic Factors", BJOG an International Journal of Obstetrics & Gynaecology, vol. 113, Issue 10, Oct. 2006, pp. 1210-1217.

Escobar-Morreale, Héctor F., "Polycystic Ovary Syndrome: Definition, Aetiology, Diagnosis and Treatment", Nature Reviews Endocrinology, vol. 14, No. 5, 2018, pp. 1-15.

Gainder et al., "Update on Management of Polycystic Ovarian Syndrome for Dermatologists", Indian Dermatology Online Journal, vol. 10, Issue 2, Mar.-Apr. 2019, pp. 97-105.

Lizneva et al., "Criteria, Prevalence, and Phenotypes of Polycystic Ovary Syndrome", Fertility and Sterility, vol. 106, No. 1, Jul. 2016, pp. 6-15.

Rosenfield, Robert L., "The Diagnosis of Polycystic Ovary Syndrome in Adolescents", Pediatrics, vol. 136, No. 6, Dec. 1, 2015, pp. 1154-1165.

Sirmans et al., "Epidemiology, Diagnosis, and Management of Polycystic Ovary Syndrome", Clinical Epidemiology, vol. 6, Dec. 18, 2013, pp. 1-13.

Williams et al., "Diagnosis and Treatment of Polycystic Ovary Syndrome", American Family Physician, vol. 94, No. 2, Jul. 15, 2016, pp. 106-113.

Wolf et al., "Geographical Prevalence of Polycystic Ovary Syndrome as Determined by Region and Race/Ethnicity", International Journal of Environmental Research and Public Health, vol. 15, No. 11, 2589, Nov. 2018, pp. 1-13.

* cited by examiner

WORKFLOW PCOS

PCOS: POSITIVE ▼  
  HIGH RISK FOR PCOS  
  NOT PCOS  
  POSITIVE

AGE: ___ — 404

SUBMIT

ETHNICITY: ___ — 416

400 — 402

TREATMENT — 408    TRACKING GRAPH — 406

CHARACTERISTIC DATA — 410

FAMILY HISTORY: POSITIVE

BMI: 28

PHYSICAL ACTIVITY: NOT ACTIVE

STRESS LEVEL: HIGH

MENARCHE AGE: 14 YEARS

MENSTRUAL PERIOD HISTORY: IRREGULAR LAST 6 MONTHS

LMP: 27 SEP 2019

PHYSICAL EXAMINATION DATA — 412

HIRSUTISM: PRESENT WITH FACIAL HAIR

UROGENITAL SYMPTOMS: POSITIVE

VIRILIZATION: POSITIVE

BUFFALO HUMP AND PURPLE STRIAE: PRESENT

PROTRUDING JAW: PRESENT

ACNE(NOT RESPONDING TO TOPICAL T/T): PRESENT

CHANGE IN SIZE(GLOOVES AND HAT): NO

WAIST SIZE: 38 INCH

CLINICAL DIAGNOSTIC DATA — 414

BASAL 17 OHP(>10NG/ML): 6NG/ML

FREE TESTOSTERONE: 4 NG/ML

ANTIMULLERIAN HL: 4.5

USG OVARY: MULTIPLE FLUID FILLED OVARY FOUND.

*FIG. 4.*

DECISION SUPPORT APPLICATION FOR PCOS

BACKGROUND

Polycystic Ovarian syndrome (PCOS) is one of the most common endocrine and metabolic disorders in pre-menopausal women. According to some studies, including the Frontiers in Bioscience published in 2014, PCOS can be found in 6 percent to 10 percent of the female population. For example, in the United States, PCOS can be found in 4.8 to 8.0 percent of the female population. In Spain, PCOS was found in 4.8 percent of the female population. PCOS has many long-term consequences, including anovulatory infertility, insulin resistance, and cardiovascular disorders. PCOS can be diagnosed by a combination of signs and symptoms of androgen excess and ovarian dysfunction. No tool exists to aid a clinician in diagnosing this condition. Clinicians (e.g., users) must make a calculation of whether a patient has PCOS, often requiring examination of several disparate systems of patient information. Clinicians are not able to examine all patient information relating to diagnosis of PCOS at once, or simultaneously on a display. Further, no clinician facing tool exists to track the PCOS condition. There is a need to assist a physician in diagnosing PCOS. There is also a need to determine a risk level of PCOS, which may be a likelihood of a patient having the PCOS condition. The risk level of PCOS, presented with the patient information in a clinician's decision support application, is also needed.

SUMMARY

Aspects of the present disclosure aim to determine a risk level of PCOS. Alongside the risk level of PCOS, aspects of the present disclosure aim to enable a clinician to simultaneously display the risk level of PCOS with patient information. With the present invention, a clinician can diagnose and treat PCOS, preventing the short and/or long-term consequences of the condition.

Aspects may include receiving patient information of a patient, determining a patient criteria is satisfied based on the patient information, and applying a predictive diagnosis model to the patient information to determine a risk level of PCOS. The predictive diagnosis model may determine a risk level of PCOS from a plurality of risk levels. Aspects may further include causing for simultaneous display on a graphical user interface ("GUI") the risk level from the plurality of risk levels and the patient information.

BRIEF DESCRIPTION OF THE DRAWINGS

The present invention is described in detail below with reference to the attached drawing figures, wherein:

FIG. 4 depicts a graphical user interface that displays the risk level of PCOS, in accordance with an aspect of the disclosure;

DETAILED DESCRIPTION OF THE INVENTION

Figure 1A:
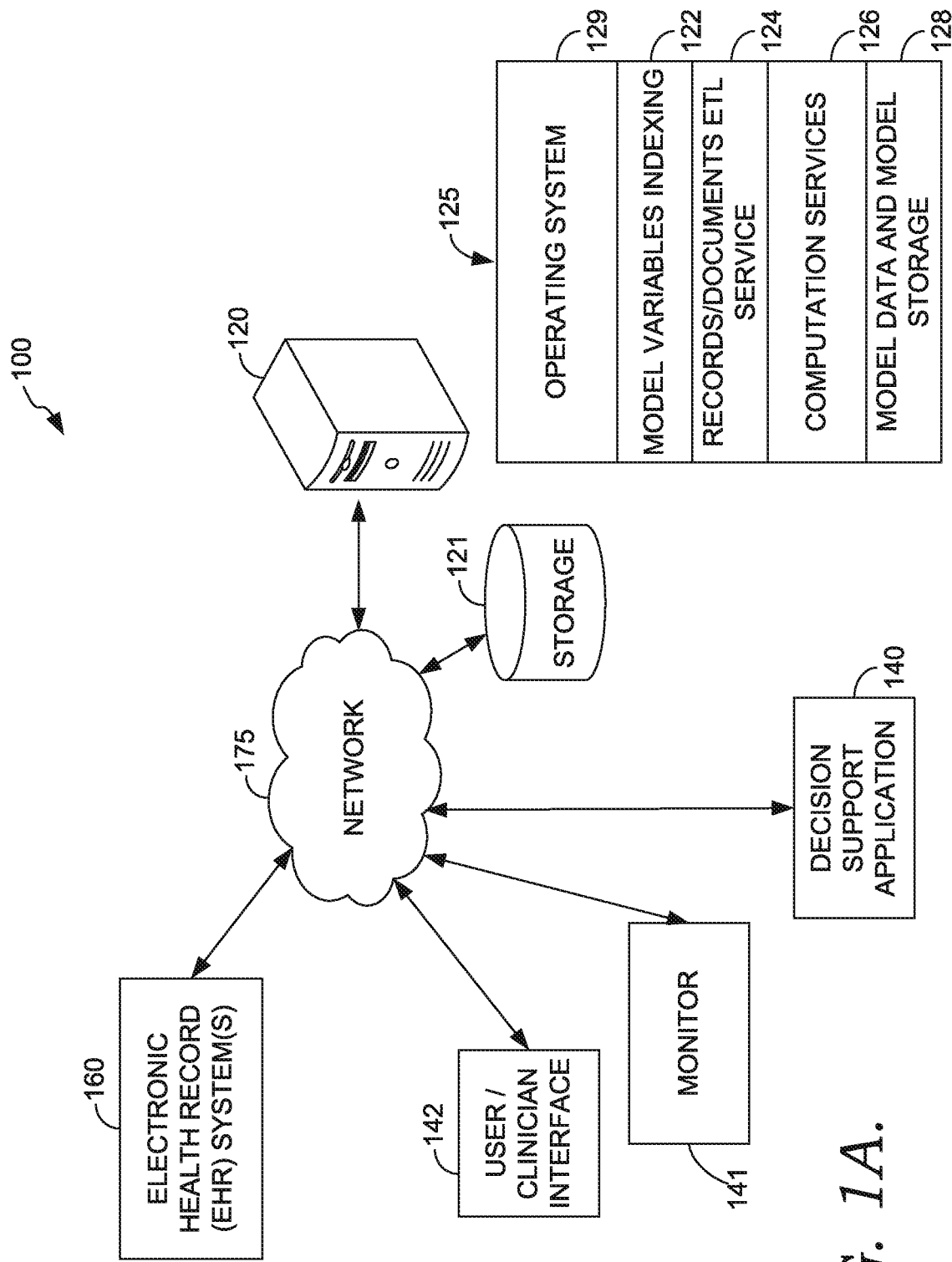
FIGS. 1A and 1B depict aspects of an illustrative operating environment suitable for practicing an aspect of the disclosure.

The subject matter of the present invention is described with specificity herein to meet statutory requirements. However, the description itself is not intended to limit the scope of this patent. Rather, the inventors have contemplated that the claimed subject matter might also be embodied in other ways, to include different blocks or combinations of blocks similar to the ones described in this document, in conjunction with other present or future technologies. Moreover, although the terms "step" and/or "block" may be used herein to connote different elements of methods employed, the terms should not be interpreted as implying any particular order among or between various blocks herein disclosed unless and except when the order of individual blocks is explicitly described.

As one skilled in the art will appreciate, aspects of the invention may be embodied as, among other things: a method, system, or set of instructions embodied on one or more computer-readable media. Accordingly, the aspects may take the form of a hardware aspect, a software aspect, or an aspect combining software and hardware. In one aspect, the invention takes the form of a computer-program product that includes computer-usable instructions embodied on one or more computer-readable media, as discussed further with respect to FIGS. 1A-1B.

Accordingly, at a high level, this disclosure describes, among other things, methods and systems for determining a risk level of PCOS. In exemplary aspects, the risk level is determined from a plurality of risk levels. Patient information of a patient may be received and comprise characteristic data, physical examination data, and clinical diagnostic data. The patient information may be received from a plurality of disparate systems. A predictive diagnosis model may be applied to the patient information to determine a risk level of PCOS from a plurality of risk levels. The risk level may be determined, as described, from the plurality of risk levels based on applying the predictive diagnosis model. On a GUI, the risk level may be simultaneously displayed with the patient information.

As previously explained, PCOS is one of the most common endocrine and metabolic disorders in pre-menopausal women. According to some studies, PCOS can be found in 6 percent to 10 percent of the female population. PCOS has many long-term consequences, including anovulatory infertility, insulin resistance, and cardiovascular disorder. Patients with PCOS are prone to health problems later in life, including diabetes and cardiovascular risk. However, despite the prevalence of this condition and the risks, PCOS is underdiagnosed. Patients diagnosed with PCOS can suffer from conditions such as infertility, diabetes, cardiovascular diseases and psychological disorders.

PCOS can be diagnosed by a combination of signs and symptoms of androgen excess and ovarian dysfunction in the absence of other specific diagnosis. Other specific diagnosis may include nonclassical congenital adrenal hyperplasia (NCCAH) and pregnancy. NCCAH may have similar conditions and indicators to those experienced by PCOS patients. Stated differently, PCOS may be diagnosed by removing NCCAH indicators and conditions. PCOS may be diagnosed using Rotterdam criteria of various aspects of the patient's condition. PCOS may be diagnosed based on a patient's history, physical examination data, and clinical diagnostic data. For example, PCOS may be diagnosed by determining a patient has a history of of anovulation and excess androgen (hirsutism).

The likelihood of a patient having the PCOS condition is referred to herein as a risk level of PCOS. The risk level of PCOS may be one of a plurality of risk levels described herein. Each risk level may describe a likelihood of the patient having the PCOS condition. A clinician may use the determined risk level to generate a diagnosis of PCOS, or may directly input the risk level of PCOS into the patient's electronic health record (EHR).

No tool exists to aid a clinician in diagnosing this condition. Clinicians (e.g., users) must make a decision of whether a patient has PCOS, often requiring examination of several disparate systems of patient information. Clinicians are not able to examine all patient information relating to diagnosis of PCOS at once. Because of this lack of tools, clinicians underdiagnose PCOS due to a lack of information. Further, no tool exists to track the PCOS condition. Tracking PCOS can help identify PCOS, and treat conditions at an early stage for the patient. In view of the risk level of PCOS and/or the tracked PCOS condition, a clinician may recommend remedial actions to prevent the chronic conditions associated with PCOS. There exists a need to determine a risk level of PCOS and present the risk level of PCOS with the patient information.

Accordingly, aspects of the present disclosure aim to determine a risk level of PCOS. Similar conditions, such as NCCAH, can influence the diagnosis of a risk level of PCOS. Therefore, in some aspects, similar conditions may be removed from the patient information to aid determining the risk level of PCOS. Alongside the risk level of PCOS, aspects of the present disclosure aim to enable a clinician to simultaneously display the risk level of PCOS with the patient information. With the present invention, a clinician may be better able to diagnose and treat PCOS, preventing short and/or long-term consequences.

Specifically, aspects may include receiving patient information of a patient comprising characteristic data, physical examination data, and clinical diagnostic data. The patient information may be received from a plurality of disparate systems (e.g., healthcare systems). Aspects may include determining a patient criteria is satisfied based on the patient information. The patient criteria may include a patient categorization based on the patient information, where one or multiple categories may satisfy the patient criteria. A predictive diagnosis model may be applied to the patient information. The predictive diagnosis model may determine a risk level of PCOS from a plurality of risk levels. The risk level from the plurality of risk levels may be determined based on applying the predictive diagnosis model. Aspects may further include causing for simultaneous display on a GUI the risk level from the plurality of risk levels and the patient information.

In another aspect, a method of causing for display a risk of polycystic ovarian syndrome may include receiving an indication of a risk level of PCOS from a plurality of risk levels based on a patient information comprising characteristic data, physical examination data, and clinical diagnostic data. The method may further include causing for simultaneous display on a GUI, the risk level from the plurality of risk levels and the patient information in a first region including the characteristic data, a second region including the physical examination data, and a third region comprising the clinical diagnostic data.

Referring now to the drawings generally and, more specifically, referring to FIG. 1A, an aspect of an operating environment 100 is provided suitable for practicing an aspect of this disclosure. Certain items in block-diagram form are shown more for being able to reference something consistent with the nature of a patent than to imply a certain component is or is not part of a certain device. Similarly, although some items are depicted in the singular form, plural items are contemplated as well (e.g., what is shown as one data store might really be multiple data stores distributed across multiple locations). But showing every variation of each item might obscure aspects of the invention. Thus, for readability, items are shown and referenced in the singular while fully contemplating, where applicable, the plural.

As shown in FIG. 1A, example operating environment 100 provides an aspect of a computerized system for compiling and/or running an aspect of a computer-decision support tool, for example, causing for display a risk level of PCOS. Environment 100 includes one or more EHR systems, such as hospital EHR system 160, communicatively coupled to network 175, which is communicatively coupled to computer system 120. In some aspects, components of environment 100 that are shown as distinct components may be embodied as part of or within other components of environment 100. For example, EHR systems 160 may comprise one or more EHR systems, such as hospital EHR systems; health information exchange EHR systems; ambulatory clinic EHR systems; and/or psychiatry/neurology EHR systems. Such EHR systems 160 may be implemented in computer system 120. Similarly, EHR system 160 may perform functions for two or more of the EHR systems (not shown).

Network 175 may comprise the Internet, and/or one or more public networks; private networks; other communications networks, such as a cellular network; or similar network for facilitating communication among devices connected through the network 175. In some aspects, network 175 may be determined based on factors such as the source and destination of the information communicated over network 175; the path between the source and destination; or the nature of the information. For example, intra-organization or internal communication may use a private network or virtual private network (VPN). Moreover, in some aspects, items shown as being communicatively coupled to network 175 may be directly communicatively coupled to other items shown communicatively coupled to network 175.

In some aspects, operating environment 100 may include a firewall (not shown) between a first component and network 175. In such aspects, the firewall may reside on a second component located between the first component and network 175, such as on a server (not shown), or reside on another component within network 175, or may reside on or as part of the first component.

Aspects of EHR system 160 include one or more data stores of health records, which may be stored on storage 121, and may further include one or more computers or servers that facilitate the storing and retrieval of health records. In some aspects, EHR system 160 may be implemented as a cloud-based platform or may be distributed across multiple physical locations. EHR system 160 may further include record systems that store real-time or near real-time patient (or user) information, such as wearable, bedside, or in-home patient monitors, for example. Although FIG. 1A depicts an exemplary EHR system 160 that may be used for storing patient information, it is contemplated that an aspect may also rely on decision support application 140 and/or monitor 141 for storing and retrieving patient record information, such as information acquired from monitor 141.

Example operating environment 100 further includes a provider user/clinician interface 142 communicatively coupled through network 175 to EHR system 160. Although environment 100 depicts an indirect communicative coupling between user/clinician interface 142 and EHR system 160 through network 175, it is contemplated that an aspect of user/clinician interface 142 is communicatively coupled to EHR system 160 directly. An aspect of user/clinician interface 142 takes the form of a GUI operated by a software application or set of applications (e.g., decision support application 140) on a computing device. In an aspect, the application includes the PowerChart® software manufactured by Cerner Corporation. In an aspect, the application is a Web-based application or applet. A healthcare provider application may facilitate causing for display a risk level of PCOS. Aspects of user/clinician interface 142 also facilitate accessing and receiving information from a display of PCOS described herein; or other health-related information, and facilitates the display of results, recommendations, or orders, for example. In an aspect, user/clinician interface 142 also facilitates receiving orders, such as orders for more resources, from a user based on the risk level of PCOS.

An aspect of decision support application 140 comprises a software application or set of applications, which may include programs, routines, functions, or computer-performed services, residing on a client computing device, on one or more servers in the cloud, or distributed in the cloud and on a client computing device, such as a personal computer, laptop, smartphone, tablet, mobile computing device, front-end terminals in communication with back-end computing systems or other computing device(s) such as computing system 120 described below. In an aspect, decision support application 140 includes a Web-based application or applet (or set of applications) usable to provide or manage user services provided by an aspect of the invention. For example, in an aspect, decision support application 140 facilitates processing, interpreting, accessing, storing, retrieving, and communicating information acquired from monitor 141, EHR system 160, or storage 121, including predictions and condition evaluations determined by aspects of the invention as described herein. In an aspect, decision support application 140 sends a recommendation or notification, such as an alarm or other indication, directly to user/clinician interface 142 through network 175. In an aspect, application 140 sends a maintenance indication to user/clinician interface 142. In some aspects, application 140 includes or is incorporated into a computerized decision support tool, as described herein. Further, some aspects of application 140 utilize user/clinician interface 142. For instance, in one aspect of application 140, an interface component, such as user/clinician interface 142, may be used to facilitate access by a user, including a clinician/caregiver or patient, to functions or information on monitor 141, such as operational settings or parameters, user identification, user data stored on monitor 141, and diagnostic services or firmware updates for monitor 141, for example.

In some aspects, application 140 and/or interface 142 facilitates accessing and receiving information from a user or health care provider about a specific patient, a set of patients, or a population according to the aspects presented herein. Such information may include historical data; health care resource data; variables measurements, time series, characteristic data, physical examination data, and clinical diagnostic data described herein; or other health-related information. Application 140 and/or interface 142 also facilitates the display of results, recommendations, or orders, for example.

As shown in example environment 100, in one aspect, decision support application 140, or the computer system on which it operates, is communicatively coupled to monitor 141 via network 175. In an aspect, patient monitor 141 communicates directly, or via network 175, to computer system 120 and/or user/clinician interface 142. In an aspect, monitor 141, which is sometimes referred to herein as an patient-interface component, comprises one or more sensor components operable to acquire patient information about a patient, such as clinical information associated with a particular physical and/or mental state of the patient. Such patient information may be acquired by monitor 141 periodically, continuously, as needed. It is also contemplated the characteristic data, physical examination data, and clinical diagnostic data be received from a patient's historical data in EHR system 160, or from human measurements, human observations, or automatically determined by sensors in proximity to the patient.

An aspect of monitor 141 stores user-derived data locally or communicates data over network 175 to be stored remotely. In an aspect, decision support application 140, or the computer system it is operating on, is wirelessly communicatively coupled to monitor 141. Application 140 may also be embodied as a software application or app operating on a user's mobile device, as described above. In an aspect, application 140 and monitor 141 are functional components of the same device, such as a device comprising a sensor, application, and a user interface. In an aspect, decision support application 140 is in communication with or resides on a computing system that is embodied as a base station, which may also include functionality for charging monitor 141 or downloading information from monitor 141.

Example operating environment 100 further includes computer system 120, which may take the form of a server, which is communicatively coupled through network 175 to EHR system 160, and storage 121. Computer system 120 comprises one or more processors operable to receive instructions and process them accordingly and may be embodied as a single computing device or multiple computing devices communicatively coupled to each other. In one aspect, processing actions performed by computer system 120 are distributed among multiple locations such as one or more local clients and one or more remote servers and may be distributed across the other components of example operating environment 100. In one aspect, computer system 120 comprises one or more computing devices, such as a server, desktop computer, laptop, or tablet, cloud-computing device or distributed computing architecture, a portable computing device such as a laptop, tablet, ultra-mobile PC, or a mobile phone.

Aspects of computer system 120 include computer software stack 125, which, in some aspects, operates in the cloud as a distributed system on a virtualization layer within computer system 120, and includes operating system 129. Operating system 129 may be implemented as a platform in the cloud and is capable of hosting a number of services, such as services 122, 124, 126, and 128, described further herein. Some aspects of operating system 129 comprise a distributed adaptive agent operating system. Aspects of services 122, 124, 126, and 128 run as a local or distributed stack in the cloud; on one or more personal computers or servers, such as computer system 120; and/or a computing device running interface 142 and/or decision support application 140. In some aspects, user/clinician interface 142 and/or decision support application 140 operate in conjunction with software stack 125.

Computation services 126 perform software operations. In an aspect, computation services 126 and records/documents service 124 include computer software services or computer-program routines. Computation services 126 also may include natural language processing services (not shown), such as Discern nCode™ developed by Cerner Corporation, or similar services. In an aspect, computation services 126 include the services or routines that may be embodied as one or more software agents or computer software routines. Computation services 126 also may include services or routines for utilizing performing sequential modeling using one or more models, including decision trees and logistic models, for determining a risk level of PCOS, such as the models described in connection to FIGS. 2-4.

In some aspects, stack 125 includes file system or cloud-services 128. Some aspects of file system/cloud-services 128 may comprise an Apache Hadoop and Hbase framework or similar frameworks operable for providing a distributed file system and which, in some aspects, provide access to cloud-based services, such as those provided by Cerner HealtheIntent®. Additionally, some aspects of file system/cloud-services 128 or stack 125 may comprise one or more stream processing services (not shown). For example, such stream processing services may be embodied using IBM InfoSphere stream processing platform; Twitter Storm stream processing; Ptolemy or Kepler stream processing software; or similar complex event processing (CEP) platforms, frameworks, or services, which may include the use of multiple such stream processing services in parallel, serially, or operating independently. Some aspects of the invention also may be used in conjunction with Cerner Millennium®, Cerner CareAware® (including CareAware iBus®), Cerner CareCompass®, or similar products and services.

Example operating environment 100 also includes storage 121 (or data store 121), which, in some aspects, includes patient data for a candidate or target patient (or information for multiple patients), including raw and processed patient data; variables associated with patient data; patient knowledge base; predictive diagnosis model; and/or patient criteria; and other similar information including data and computer-usable instructions.

Additionally, it is contemplated that the term "data" used herein includes any information that can be stored in a computer storage device or system, such as user-derived data, computer-usable instructions, software applications, or other information. In some aspects, storage 121 comprises data store(s) associated with EHR system 160. Further, although depicted as a single storage store, storage 121 may comprise one or more data stores (e.g., from disparate systems), or may be in the cloud.

Figure 1B:
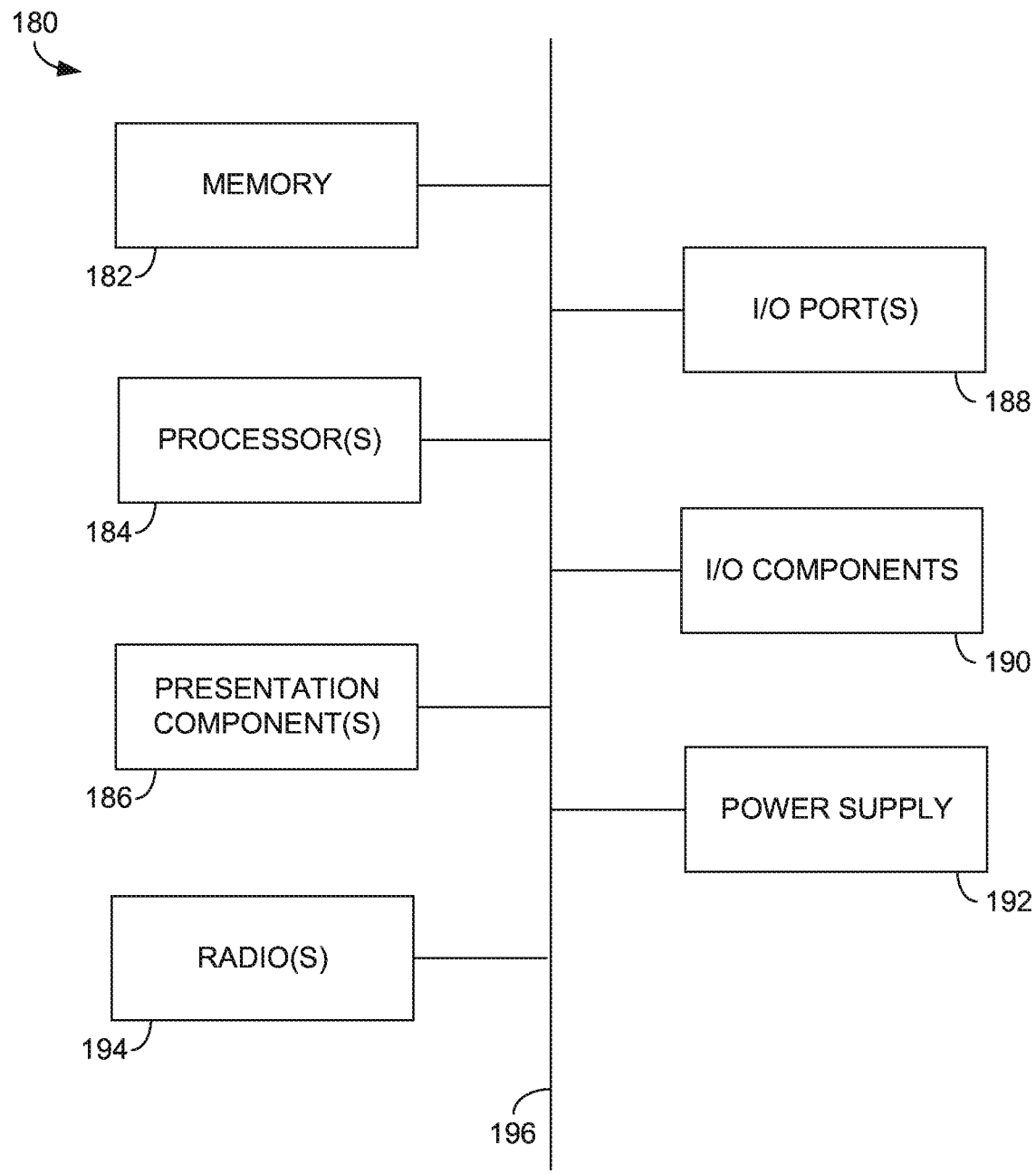

Turning briefly to FIG. 1B, there is shown one example aspect of computing system 180 representative of a system architecture that is suitable for computer systems, such as computer system 120. Computing system 180 includes a bus 196 that directly or indirectly couples the following devices: memory 182; one or more processors 184; one or more presentation components 186; input/output (I/O) ports 188; I/O components 190; radio 194; and an illustrative power supply 192. Bus 196 represents what may be one or more busses, such as an address bus, data bus, or combination thereof. Although the various blocks of FIG. 1A are shown with lines for the sake of clarity, in reality, delineating various components is not so clear and, metaphorically, the lines would more accurately be grey and fuzzy. For example, one may consider a presentation component, such as a display device, to be an I/O component. However, processors also have memory. As such, the diagram of FIG. 1A is merely illustrative of an exemplary computing system that can be used in connection with one or more aspects of the present invention. Distinction is not made between such categories as "workstation," "server," "laptop," "hand-held device," etc., as all are contemplated within the scope of FIG. 1A and reference to "computing system."

Computing system 180 typically includes a variety of computer-readable media. Computer-readable media can be any available media that can be accessed by computing system 180 and includes both volatile and nonvolatile media, and removable and non-removable media. By way of example, and not limitation, computer-readable media may comprise computer storage media and communication media. Computer storage media includes both volatile and nonvolatile, removable and non-removable media implemented in any method or technology for storage of information, such as computer-readable instructions, data structures, program modules, or other data. Computer storage media includes, but is not limited to, RAM, ROM, EEPROM, flash memory, or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing system 180. Computer storage media does not comprise signals, per se. Communication media typically embodies computer-readable instructions, data structures, program modules or other data in a modulated data signal, such as a carrier wave or other transport mechanism and includes any information delivery media. The term "modulated data signal" means a signal that has one or more of its characteristics set or changed in such a manner as to encode information in the signal. By way of example, and not limitation, communication media includes wired media, such as a wired network or direct-wired connection, and wireless media, such as acoustic, RF, infrared and other wireless media. Combinations of any of the above should also be included within the scope of computer-readable media.

Memory 182 includes computer storage media in the form of volatile and/or nonvolatile memory. The memory may be removable, non-removable, or a combination thereof. Exemplary hardware devices include solid-state memory, hard drives, optical-disc drives, and etc. Computing system 180 includes one or more processors that read data from various entities, such as memory 182 or I/O components 190. Presentation component(s) 186 present data indications to a user or other device. Exemplary presentation components include a display device, speaker, printing component, vibrating component, and etc.

In some aspects, computing system 180 comprises radio (s) 194 that facilitates communication with a wireless telecommunications network. Illustrative wireless telecommunications technologies include CDMA, GPRS, TDMA, GSM, and the like. Radio(s) 194 may additionally or alternatively facilitate other types of wireless communications, including Wi-Fi, WiMAX, LTE, or other VoIP communications. As can be appreciated, in various aspects, radio(s) 194 can be configured to support multiple technologies and/or multiple radios can be utilized to support multiple technologies.

I/O ports 188 allow computing system 180 to be logically coupled to other devices, including I/O components 190, some of which may be built in. Illustrative components include a microphone, joystick, game pad, satellite dish, scanner, printer, wireless device, and etc. The I/O components 190 may provide a natural user interface (NUI) that processes air gestures, voice, or other physiological inputs generated by a user. In some instances, inputs may be transmitted to an appropriate network element for further processing. An NUI may implement any combination of speech recognition; stylus recognition; facial recognition; biometric recognition; gesture recognition, both on screen and adjacent to the screen; air gestures; head and eye tracking; and touch recognition (as described in more detail below) associated with a display of the computing system 180. The computing system 180 may be equipped with depth cameras, such as stereoscopic camera systems; infrared camera systems; RGB camera systems; touchscreen technology; and combinations of these, for gesture detection and recognition. Additionally, the computing system 180 may be equipped with accelerometers or gyroscopes that enable detection of motion.

The architecture depicted in FIG. 1B is provided as one example of any number of suitable computer architectures, such as computing architectures that support local, distributed, or cloud-based software platforms, and are suitable for supporting computer system 120.

Returning to FIG. 1A, in some aspects, computer system 120 is a computing system made up of one or more computing devices. In some aspects, computer system 120 includes one or more software agents and, in an aspect, includes an adaptive multi-agent operating system, but it will be appreciated that computer system 120 may also take the form of an adaptive single agent system or a non-agent system. Computer system 120 may be a distributed computing system; a data processing system; a centralized computing system; a single computer, such as a desktop or laptop computer; or a networked computing system.

Figure 2:
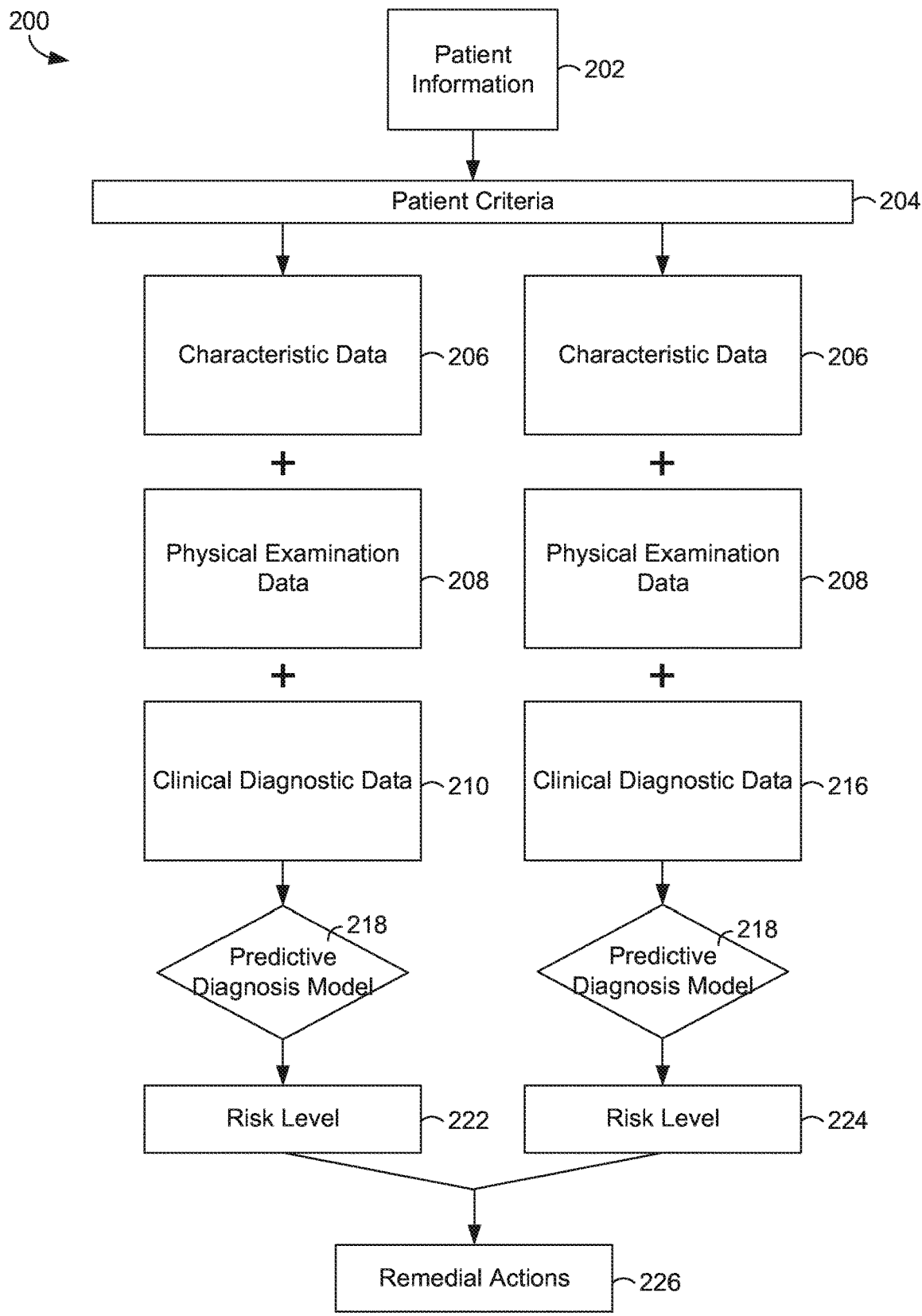
FIGS. 2 and 3 depict a flow diagram of a method for determining a risk level of PCOS, in accordance with an aspect of the disclosure.

Turning now to FIG. 2, it depicts a flow diagram of a method 200 for determining a risk level of PCOS. In particular, example method 200 may be implemented by computation services 126 and/or on a decision support application 140 as described in FIG. 1.

In accordance with method 200, patient information 202 may be received. In some aspects, the patient information 202 may be received from systems such as the EHR systems 160 and/or user clinician interface 142, as described in FIG. 1. In some aspects, the patient information 202 may be received from a plurality of disparate systems. Each of the disparate systems may not be in communication with one another, for example, from a plurality of healthcare facilities and/or plurality of healthcare providers.

It may be determined patient criteria 204 is satisfied based on the patient information 202. The patient criteria 204 may be any element of the patient information 202 about the patient. For example, in some aspects, the patient criteria 204 may include a reproductive age for the patient and/or an indication of whether menstruation has started for the patient. The patient criteria 204 may be an adolescent female from the onset of menstruation with an additional two years until the patient is 18 years of age. The patient criteria 204 may be a reproductive female from ages 18 to 45 years of age, or from ages 18 to menopause. For example, in embodiments where the patient criteria may include a patient categorization based on the patient information, one category may be whether the patient has started to menstruate, and an indication in the patient information 202 may indicate the onset of menstruation for the patient.

Based on the patient criteria 204, predictive diagnosis model 218 may be applied to the patient information 202, which may include characteristic data 206, physical examination data 208, clinical diagnostic data 210, or clinical diagnostic data 216 (described below).

The patient information 202 may include characteristic data 206, physical examination data 208, and/or clinical diagnostic data 210 or 216. In some aspects, described herein, the patient information 202 may depend on the patient criteria 204. The characteristic data 206 may include any characteristics of a patient (e.g., race, age, family history of PCOS, and prior visit data). For example, the characteristic data 206 or 212 may include patient historical data and/or patient demographic information. The physical examination data 208 may include any subjective symptoms of PCOS. For example, the physical examination data 208 may include visual indicia, androgen indicators, and/or genital discomfort (e.g., urogenital complaints). The clinical diagnostic data 210 and 216 may include any objective symptoms of PCOS. For example, the clinical diagnostic data 210 and 216 may include imaging data, hormone levels, and/or a fertility indicators.

The predictive diagnosis model 218 may be applied to the patient information 202 to determine a risk level 222 or 224 respectively. The patient information 202 applied to the predictive diagnosis model 218 may be different dependent on the patient criteria 204 satisfied. The clinical diagnostic data 210 may be different than clinical diagnostic data 216 dependent on the patient criteria 204 that are satisfied. In some aspects, only the clinical diagnostic data 210 may be different than the clinical diagnostic data 216. For example, the clinical diagnostic data 210 may include biochemical finding and imaging data. Clinical diagnostic data 210 may include biochemical finding and imaging data (for example, imaging data 310 illustrated in FIG. 3). The imaging data may include any sound or radiation imaging data. In some embodiments, the clinical diagnostic data 216 and 210 may vary due to the patient criteria 204. For example, if a patient is an adolescent, imaging data may not be available or relevant to determinations of a risk level of PCOS.

In one aspect, the patient criteria 204 may be a patient below 18 years of age. A patient may have patient information 202 that satisfies the patient criteria 204 (the patient may be 16 years old). Patient information 202 may be applied to the predictive diagnosis model 218. The patient information may comprise characteristic data 206, physical examination data 208, and clinical diagnostic data 210, which may be applied to the predictive diagnosis model 218. The predictive diagnosis model 218 may determine a risk level 224 of PCOS for the patient.

A predictive diagnosis model 218 may be applied to the patient information 202. The predictive diagnosis model 218 may determine a risk level 222 or 224 of PCOS from a plurality of risk levels. The predictive diagnosis model 218 may include a plurality of risk levels and criteria associated with each risk level. When the predictive diagnosis model 218 is applied, the patient information 202 may be compared to the patient criteria 204, described herein.

The predictive diagnosis model 216 may include a Rotterdam criteria of the patient information 202 to determine a risk level 222 or 224. For example, the Rotterdam criteria may include the determination that a number of aspects of the patient information 202 are above a normal threshold for the patient. For example, the Rotterdam criteria may include a determination that one aspect of at least two of the characteristic data 206, physical examination data 208, and/or clinical diagnostic data 210 or 216 are above a normal threshold for the patient. The normal threshold may be determined based on the patient information 202 for an identified "average" patient with no risk of PCOS. In some aspects, the predictive diagnosis model 216 may determine the risk levels 222 or 224. The risk levels 222 or 224 may be determined based on the number of aspects satisfied by the Rotterdam criteria. For example, if the characteristic data 206 and physical examination data 208 are above a normal threshold for a patient, the patient may be determined to be of a high risk level of PCOS. If the characteristic data 206, physical examination data 208, and clinical diagnostic data 210 or 216 are above a normal threshold for a patient, the patient may be determined to be certain of having PCOS.

The risk level 222 or 224 from the plurality of risk levels may be determined based on applying the predictive diagnosis model 218. As described herein, determining the risk level 222 and 224 may include determining the patient information 202 satisfies criteria of a risk level 222 or 224. If multiple risk levels are satisfied, determining the risk level may include determining the highest rating of risk of the plurality of risk levels.

Aspects may further include causing for simultaneous display on a GUI the risk level from the plurality of risk levels and the patient information. In some aspects, remedial actions 226 may be simultaneously displayed on the GUI based on the risk level 222 or 224. Remedial actions 226 may include regular visits and monitoring, discussing long-term consequences, and lifestyle modifications. Remedial actions 226 may also include lifestyle modification and treatment.

Figure 3:
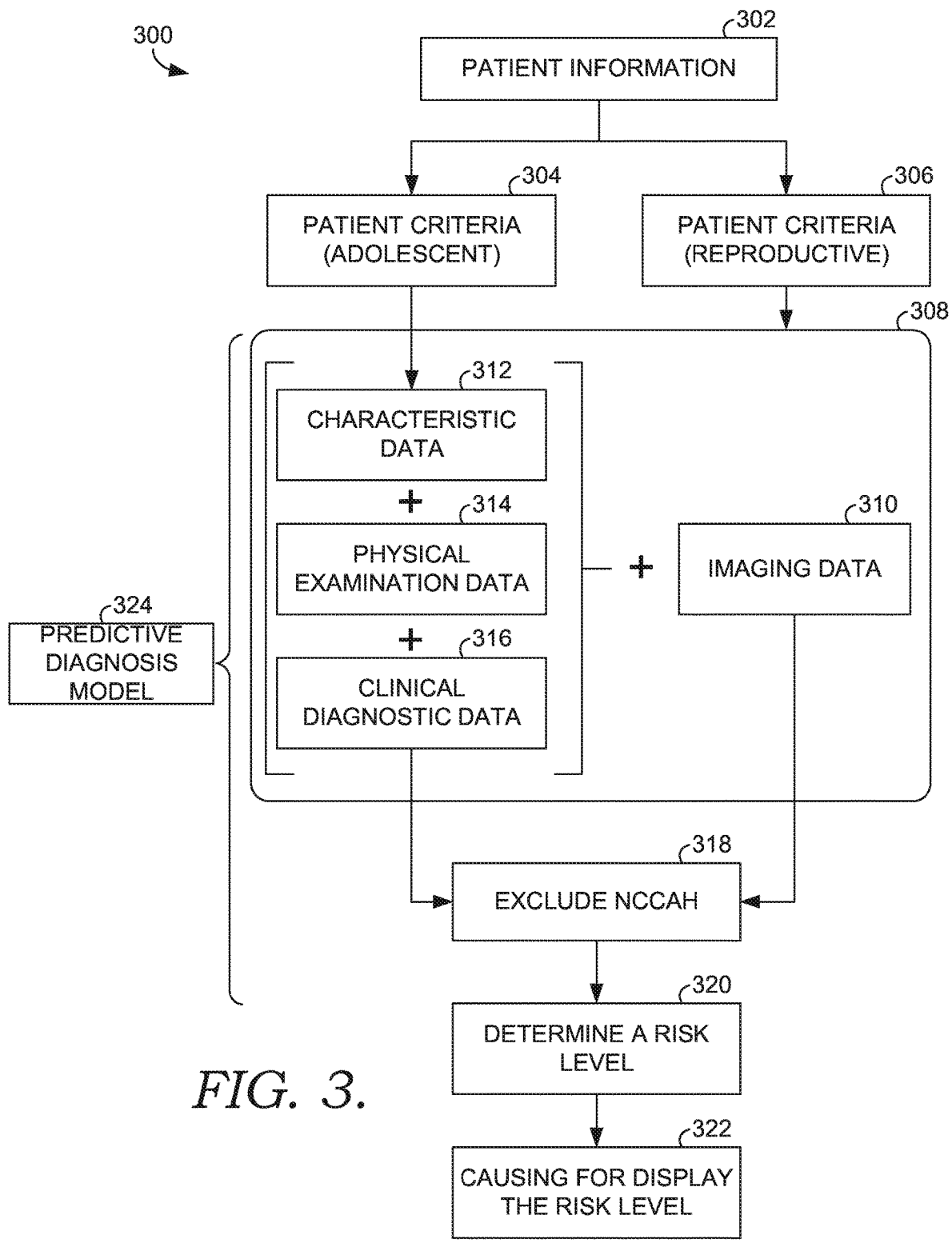

FIG. 3 depicts a flow diagram of one aspect of a method 300 for determining a risk level of PCOS. Patient information 302 may be received about a patient. The patient information may satisfy the patient criteria 304 or the patient criteria 306. Dependent on the patient criteria 304 or 306 satisfied, the patient information 302 applied to the predictive diagnosis model 324 may be changed.

Two different sets of patient information 302 are depicted in FIG. 3. The sets of patient information 302 may depend on the patient criteria 304 and 306. For example, when patient criteria 304 is satisfied, the patient information 302 may include characteristic data 312, physical examination data 314, and clinical diagnostic data 316. If the patient criteria 306 is satisfied, the patient information 302 may include the data block 308, and apply it to the predictive diagnosis model 324. The data block 308 may include characteristic data 312, physical examination data 314, clinical diagnostic data 316, and imaging data 310. In some aspects, imaging data 310 may include any sound or radiation imaging data. For example, imaging data 310 may include x-rays, or ultrasonography (USG) of ovary and thyroid function, and may include testing prolactin level and FSH level. In some aspects, patient information related to NCCAH is excluded 318.

As described herein, imaging data 310 may not be applied to the predictive diagnosis model 324 dependent on the patient criteria 304 and 306. For a reproductive patient, as described for patient criteria 306, imaging data 310 may be available and relevant to a determination of a risk level of PCOS. By excluding imaging data 310 from predictive diagnosis model 324 for some patient criteria, unavailable patient information 302 or irrelevant patient information 302 may not be evaluated, making the predictive diagnosis model 324 more accurate.

The patient information 302, described above, may be applied to the predictive diagnosis model 324. The predictive diagnosis model 324 may determine a risk level 320 of PCOS from a plurality of risk levels. The risk level may be caused for display 322.

FIG. 4 depicts a GUI 400 that displays the risk level of PCOS. The graphical user interface 400 illustrates various aspects of the present disclosure caused for simultaneous display. A plurality of risk levels 402, age 404, tracking graph 406, treatment 408, first region 410, second region 412, third region 414, and ethnicity 416 are illustrated on the GUI 400.

The plurality of risk levels 402 illustrate one aspect of the present disclosure, where the risk levels 402 include three risk levels: high risk for PCOS; not PCOS; and positive. The high risk for PCOS may indicate a high risk level for PCOS. Stated differently, high risk for PCOS may indicate the patient likely has the PCOS condition. Not PCOS may indicate a low risk level for PCOS; or the patient may have low to no risk level of PCOS. Positive may indicate the patient is certain (e.g., 100% likely) to have PCOS.

As illustrated, in some aspects, the top risk level of the plurality of risk levels 402 may indicate the risk level determined by applying the patient information to the predictive diagnosis model, described herein. Stated differently, the determined risk level may be prepopulated on the GUI 400 for a patient. The risk level may be determined as positive, and prepopulate the GUI 400. In some aspects, a clinician may submit the determined risk level to the patient's EHR, and/or select a different risk level from the plurality of risk levels 402 to submit to the patient's EHR.

The patients age 404 and ethnicity 416 may be simultaneously displayed on the GUI 400. In some aspects, the patient's ethnicity 416 can be a factor in determining the patient's risk level of PCOS. Similarly, the patient's age 404 may be a factor in determining the risk level of PCOS. Information about age or ethnicity may be simultaneously displayed to aid a caregiver in diagnosing PCOS.

A tracking graph 406 icon may be simultaneously displayed on the GUI 400. The tracking graph 406 may track clinical diagnostic data 414 over time. A clinician may interact with the tracking graph 406 to aid diagnosis of PCOS. In some aspects, selecting the tracking graph 406 may generate on the GUI an example clinical diagnostic over time as described in FIG. 5.

Treatment 408 may also be presented as an icon simultaneously on the GUI 400. Treatment 408 may, when activated, display remedial actions for a clinician, as described herein. In this way, a clinician may reference remedial actions quickly and on the same screen as other relevant information.

First region 410, second region 412, and third region 414 may be simultaneously displayed with the risk level as shown in FIG. 4. In some aspects, the first region 410 may include characteristic data. In some aspects, the second region 412 may include the physical examination data. In some aspects, the third region 414 may include the clinical diagnostic data. The first region 410, second region 412, and third region 414 may display the patient information. The patient information displayed in the first region 410, second region 412, and third region 414 may be caused for display in real-time or near real-time. For example, the patient information may be displayed as data is updated, input, and recorded to the patient's EHR.

Characteristic data 410, physical examination data 412, and clinical diagnostic data 414 may be simultaneously displayed with the risk level as shown in FIG. 4. In some aspects each of the characteristic data 410, physical examination data 412, and clinical diagnostic data 414 may be displayed in real-time.

Figure 5:
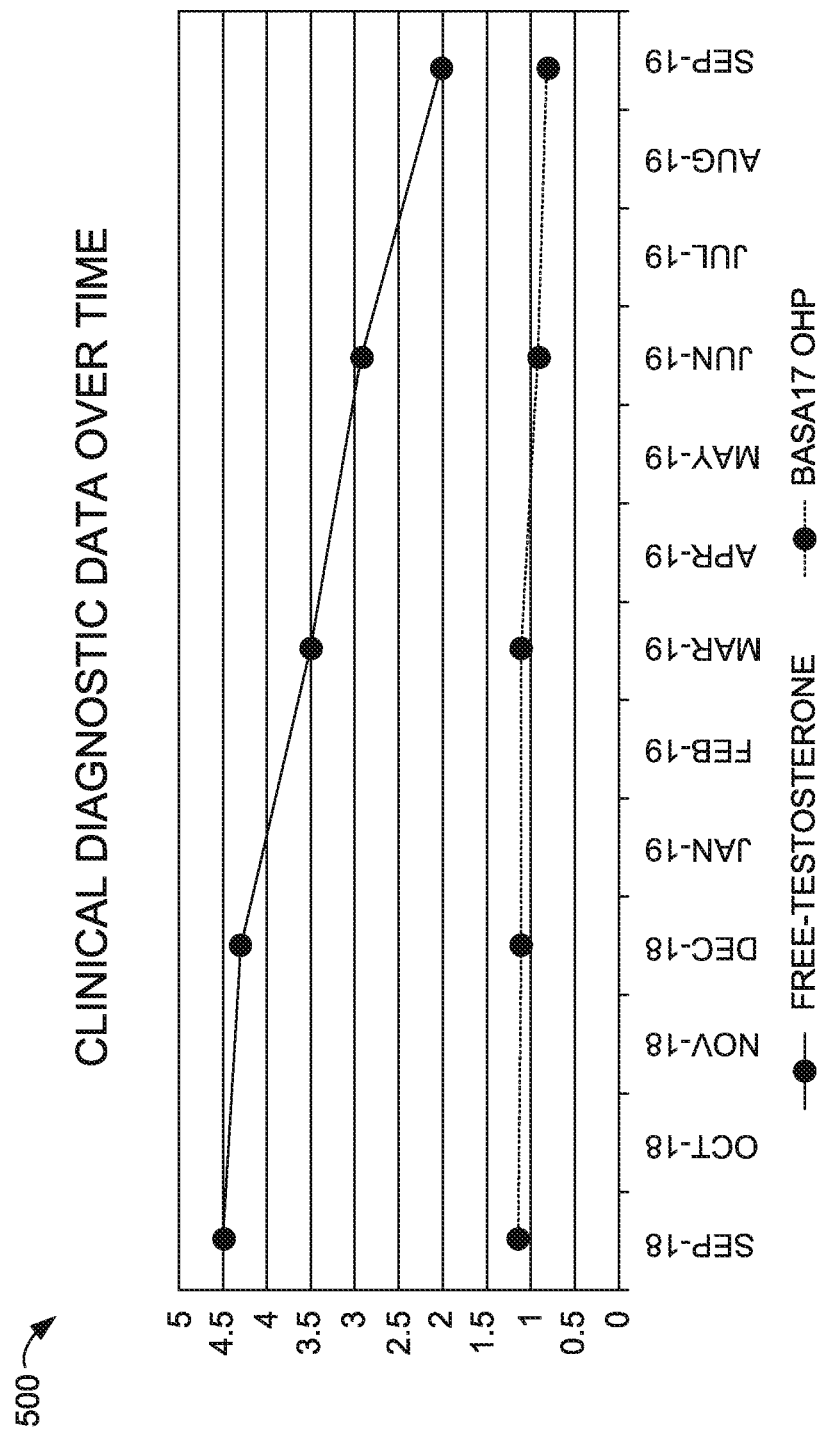
FIG. 5 depicts a graphical user interface that displays the clinical diagnostic data, in accordance with an aspect of the disclosure.

FIG. 5 depicts a graphical user interface 500 that displays the clinical diagnostic data over time. In some aspects, if a patient is at risk level of PCOS, a remedial action may be to bring some hormones into a normal range. To track the progress of treatments, the clinical diagnostic may be tracked over time, shown in one aspect here. Each visit to a clinician and/or measurement of the hormone may be illustrated with an indicator, such as a black dot, as illustrated.

Figure 6:
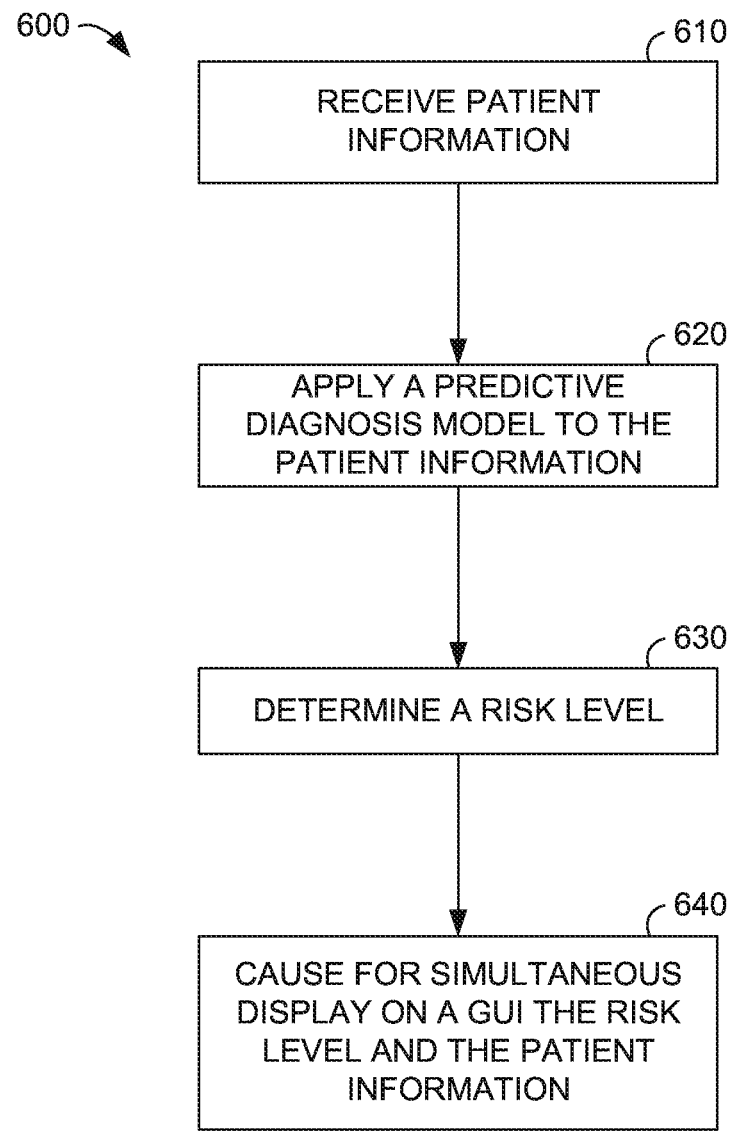
FIG. 6 is a flow diagram showing an example of determining a risk level of PCOS, in accordance with aspects of the present disclosure.

FIG. 6 is a flow diagram showing an example method 600 of determining a risk level of PCOS. Method 600 may be performed by any computing device, such as computing device described with respect to FIGS. 1A and 1B.

Initially, at block 610, the method 600 may include receive patient information. For example, receiving patient information of a patient comprising characteristic data, physical examination data, and clinical diagnostic data. In some aspects, the patient information may be received from a patient's EHR, as described herein.

At block 620, the method 600 may include applying a predictive diagnosis model to the patient information. For example, a predictive diagnosis model may be applied to the patient information to determine a risk level of PCOS from a plurality of risk levels.

At block 630, the method 600 may include determining a risk level. For example, applying the predictive diagnosis model to determine a risk level from the plurality of risk levels.

At block 640, the method 600 may include causing for simultaneous display on a GUI the risk level and the patient information. For example, causing for simultaneous display on a GUI the risk level from the plurality of risk levels and the patient information. In some embodiments, further cause for simultaneous display may be remedial actions and/or the plurality of risk levels.

Figure 7:
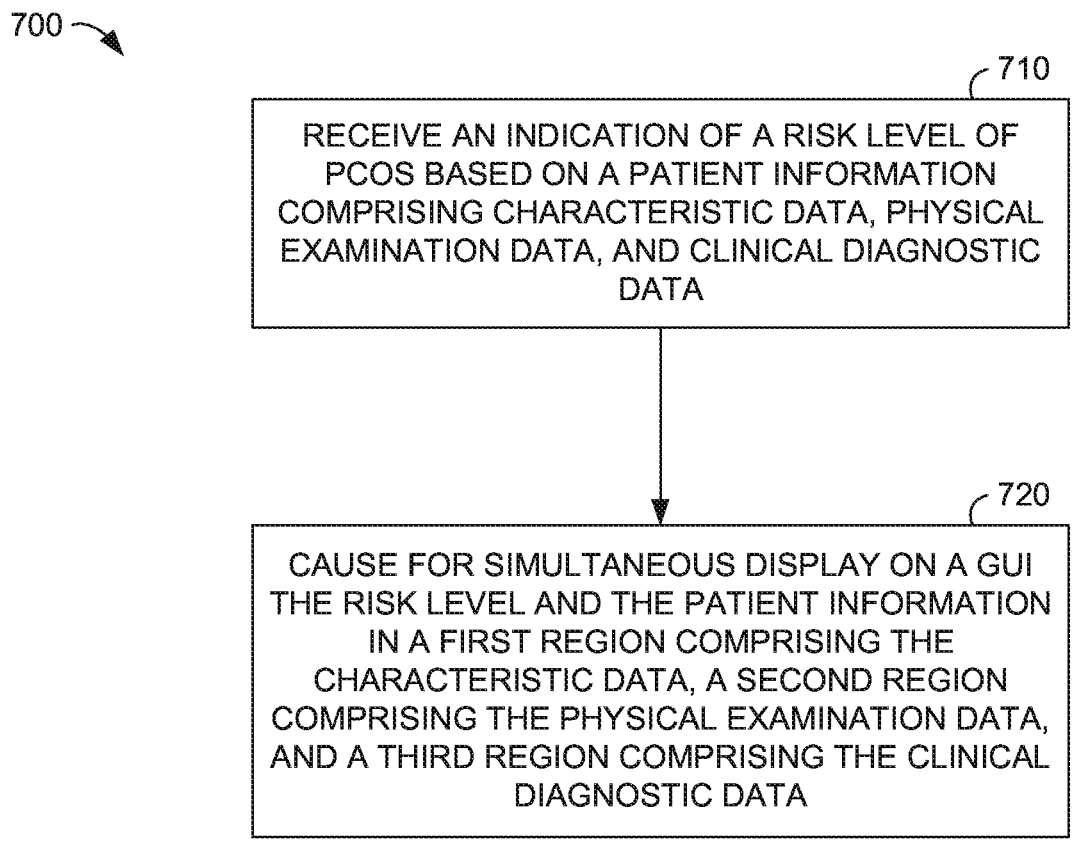
FIG. 7 is a flow diagram showing an example of a method of receiving an indication of a risk level of PCOS and causing for display the risk level, in accordance with aspects of the present disclosure.

FIG. 7 is a flow diagram showing an example of a method 700 receiving an indication of a risk level of PCOS and causing for display the risk level.

At block 710, the method 700 may include receiving an indication of a risk level of PCOS based on a patient information comprising characteristic data, physical examination data, and clinical diagnostic data. For example, receiving an indication of a risk level of PCOS from a plurality of risk levels based on patient information comprising characteristic data, physical examination data, and clinical diagnostic data.

At block 720, the method 700 may include causing for simultaneous display on a GUI the risk level and the patient information in a first region comprising the characteristic data, a second region comprising the physical examination data, and a third region comprising the clinical diagnostic data. For example, causing for simultaneous display on a GUI the risk level from the plurality of risk levels, and the patient information in a first region comprising the characteristic data, a second region comprising the physical examination data, and a third region comprising the clinical diagnostic data.

Figure 8:
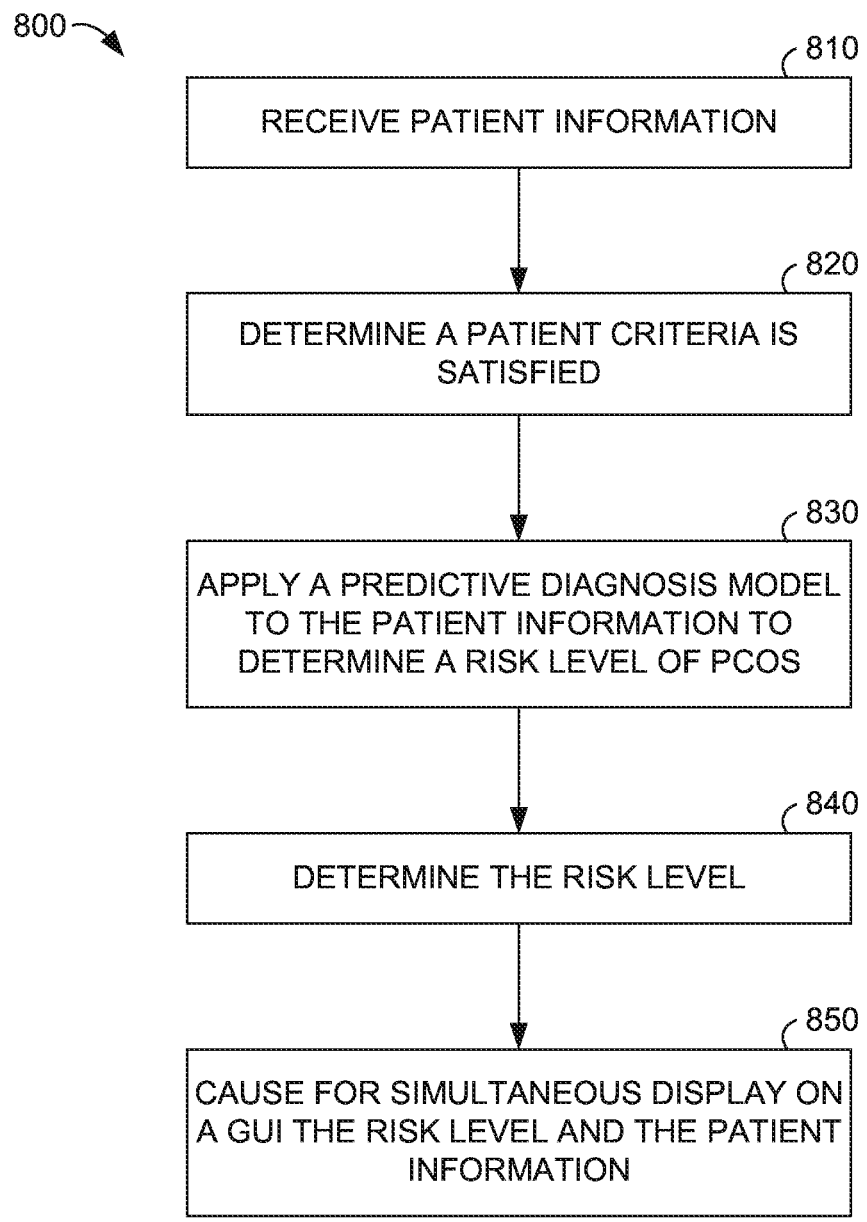
FIG. 8 is a flow diagram showing an example of determining a risk level of PCOS, in accordance with aspects of the present disclosure.

FIG. 8 is a flow diagram showing an example method 800 of determining a risk level of PCOS. The method 800 may include block 810, receive patient information. For example, receive patient information of a patient comprising characteristic data, physical examination data, and clinical diagnostic data from a remote server.

The method 800 may include block 820, determine a patient criteria is satisfied. For example, determining a patient criteria is satisfied based on the patient information.

At block 830, the method 800 may include applying a predictive diagnosis model to the patient information to determine a risk level of PCOS. For example, based on the satisfied patient criteria, applying a predictive diagnosis model to the patient information to determine a risk level of PCOS from a plurality of risk levels.

At block 840, the method 800 may include determining the risk level. For example, determining the risk level from the plurality of risk levels based on applying the predictive diagnosis model to the patient information.

The method 800 may include block 850, cause for simultaneous display on a GUI the risk level and the patient information. For example, causing for simultaneous display on a GUI the risk level from the plurality of risk levels and the patient information.

Many different arrangements of the various components depicted, as well as components not shown, are possible without departing from the spirit and scope of the present invention. It will be understood that certain features and sub-combinations are of utility and may be employed without reference to other features and sub-combinations and are contemplated within the scope of the claims. Not all steps listed in the various figures need be carried out in the specific order described. Accordingly, the scope of the invention is intended to be limited only by the following claims.

What is claimed is:

1. A system having one or more hardware processors configured to initiate a plurality of operations, the operations comprising:
   generating, via the one or more hardware processors, a hardware based predictive diagnosis electronic model, that includes information corresponding at least partially to a plurality of Rotterdam criteria, based on instances of data from a group comprising characteristic information, physical examination information, clinical diagnostic information, and risk level information,
      wherein the predictive diagnosis electronic model is configured, via the one or more hardware processors, based at least in part on:
         (a) instances of the data from the group comprising the characteristic information, the physical examination information, the clinical diagnostic information, and the risk level information; and
         (b) one or more decision elements, of the predictive diagnosis electronic model, indicating one or more risk levels of Polycystic Ovarian syndrome (PCOS) based on the instances of the data;
   subsequent to receiving patient information comprising a plurality of elements including characteristic data, physical examination data, and clinical diagnostic data, applying the predictive diagnosis electronic model to the patient information,
      wherein applying the predictive diagnosis electronic model to the patient information comprises:
         inputting a first set of values for the plurality of elements, representing a set of the patient information including a particular type of information, to the predictive diagnosis electronic model in response to detecting a first set of patient criteria; and inputting a second set of values for the plurality of elements, representing the set of the patient information but not including the particular type of information, to the predictive diagnosis electronic model in response to detecting a second set of patient criteria, the second set of patient criteria differing from the first set of patient criteria;

determining a risk level of PCOS based on the application of the predictive diagnosis electronic model to the patient information; and presenting, via an electronic user interface and via the one or more hardware processors, risk level information associated with the determining of the risk level of PCOS, wherein:
the risk level information includes a treatment remedial action to bring values of hormone measurements associated with the patient information into a normal range,
the risk level information further includes the determined risk level of PCOS, and
the risk level information indicates whether the first set of values representing the set of the patient information including the particular type of information was input to the predictive diagnosis electronic model during the applying.

2. The system of claim 1, wherein the patient information includes content from a plurality of disparate systems, and wherein the characteristic data comprises patient historical data associated with an electronic medical record of a patient.

3. The system of claim 1, wherein the physical examination data comprises at least one of: visual indicia, androgen indicators, and genital discomfort data.

4. The system of claim 1, wherein the clinical diagnostic data comprises at least one of: imaging data, hormone level data, or fertility indicators.

5. One or more non-transitory media having instructions that, when executed by one or more hardware processors, cause the one or more hardware processors to initiate a plurality of operations, the operations comprising:

generating, via the one or more hardware processors, a hardware based predictive diagnosis electronic model, that includes information corresponding at least partially to a plurality of Rotterdam criteria, based on instances of data from a group comprising characteristic information, physical examination information, clinical diagnostic information, and risk level information, wherein the predictive diagnosis electronic model is configured, via the one or more hardware processors, based at least in part on:
(a) instances of the data from the group comprising the characteristic information, the physical examination information, the clinical diagnostic information, and the risk level information; and
(b) one or more decision elements, of the predictive diagnosis electronic model, indicating one or more risk levels of Polycystic Ovarian syndrome (PCOS) based on the instances of the data;

subsequent to receiving patient information comprising a plurality of elements including characteristic data, physical examination data, and clinical diagnostic data, applying the predictive diagnosis electronic model to the patient information, wherein applying the predictive diagnosis electronic model to the patient information comprises:

inputting a first set of values for the plurality of elements, representing a set of the patient information including a particular type of information, to the predictive diagnosis electronic model in response to detecting a first set of patient criteria; and inputting a second set of values for the plurality of elements, representing the set of the patient information but not including the particular type of information, to the predictive diagnosis electronic model in response to detecting a second set of patient criteria, the second set of patient criteria differing from the first set of patient criteria;

determining a risk level of PCOS based on the application of the predictive diagnosis electronic model to the patient information; and presenting, via an electronic user interface and via the one or more hardware processors, risk level information associated with the determining of the risk level of PCOS, wherein:
the risk level information includes a treatment remedial action to bring values of hormone measurements associated with the patient information into a normal range,
the risk level information further includes the determined risk level of PCOS, and
the risk level information indicates whether the first set of values representing the set of the patient information including the particular type of information was input to the predictive diagnosis electronic model during the applying.

6. The one or more non-transitory media of claim 5, wherein the treatment remedial action is administered to a patient to treat the patient and prevent chronic conditions associated with PCOS.

7. The one or more non-transitory media of claim 5, wherein the treatment remedial action comprises:
applying hormone monitoring to a particular patient by:
drawing body fluid from the particular patient;
performing one or more hormone measurements on the body fluid; and
bringing hormone levels detected from the hormone measurements into a normal range for the particular patient.

8. A computer implemented method, comprising:
generating, via one or more hardware processors, a hardware based predictive diagnosis electronic model, that includes information corresponding at least partially to a plurality of Rotterdam criteria, based on instances of data from a group comprising characteristic information, physical examination information, clinical diagnostic information, and risk level information, wherein the predictive diagnosis electronic model is configured, via the one or more hardware processors, based at least in part on:
(a) nstances of the data from the group comprising the characteristic information, the physical examination information, the clinical diagnostic information, and the risk level information; and
(b) one or more decision elements, of the predictive diagnosis electronic model, indicating one or more risk levels of Polycystic Ovarian syndrome (PCOS) based on the instances of the data;

subsequent to receiving patient information comprising a plurality of elements including characteristic data, physical examination data, and clinical diagnostic data, applying the predictive diagnosis electronic model to the patient information,
wherein applying the predictive diagnosis electronic model to the patient information comprises:
inputting a first set of values for the plurality of elements, representing a set of the patient information including a particular type of information, to the predictive diagnosis electronic model in response to detecting a first set of patient criteria; and
inputting a second set of values for the plurality of elements, representing the set of the patient information but not including the particular type of information, to the predictive diagnosis electronic model in response to detecting a second set of patient criteria, the second set of patient criteria differing from the first set of patient criteria;
determining a risk level of PCOS based on the application of the predictive diagnosis electronic model to the patient information; and
presenting, via an electronic user interface and via the one or more hardware processors, risk level information associated with the determining of the risk level of PCOS,
wherein:
the risk level information includes a treatment remedial action to bring values of hormone measurements associated with the patient information into a normal range,
the risk level information further includes the determined risk level of PCOS, and
the risk level information indicates whether the first set of values representing the set of the patient information including the particular type of information was input to the predictive diagnosis electronic model during the applying.

9. The computer implemented method of claim 8, wherein the patient information is received from a plurality of disparate systems.

10. The computer implemented method of claim 8, wherein the characteristic data comprises patient historical data received from an electronic medical record of a patient.

11. The computer implemented method of claim 8, wherein the physical examination data comprises at least one of: visual indicia, androgen indicators, and genital discomfort data.

12. The computer implemented method of claim 8, wherein the clinical diagnostic data comprises at least one of: imaging data, hormone level data, or fertility indicators.

13. The computer implemented method of claim 8, further comprising activating a sensor to collect a hormone level measurements for a patient, wherein the patient information includes the hormone level measurement, and wherein the patient criteria includes a reproductive demographic for the patient.

14. The computer implemented method of claim 8, wherein the patient information is displayed on a graphical user interface in a first region comprising the characteristic data, a second region comprising the physical examination data, and a third region comprising the clinical diagnostic data.

15. The computer implemented method of claim 8, further comprising simultaneously displaying the determined risk level of PCOS and the patient information on a graphical user interface.

16. The system of claim 1, wherein the risk level of PCOS is determined to be high in response to a particular aspect of each of two of the elements being above a normal threshold for a patient.

17. The system of claim 1, wherein the operations further comprise determining that a patient has PCOS in response to a particular aspect of each of the elements being above a normal threshold for the patient.

18. The system of claim 1, wherein a risk rating of PCOS is determined to be a first rating in response to a particular aspect of two of the elements being above a normal threshold for a patient and is determined to be a second rating in response to a particular aspect of each of the elements being above the normal threshold for the patient, and wherein the operations further comprise: selecting a highest rating as the determined risk level of PCOS.

19. The system of claim 1, wherein the risk level of PCOS is determined to be high in response to a particular aspect of each of two elements, of the plurality of elements, being above a respective normal threshold.

20. The system of claim 1, wherein the operations further comprise determining that a patient has PCOS in response to a particular aspect of each of the plurality of elements being above a respective normal threshold.

21. The system of claim 1, wherein a risk rating of PCOS is determined to be:
a first level in response to a particular aspect of each of two elements selected from a group of elements comprising the characteristic data, physical examination data, and clinical diagnostic data, of the plurality of elements, being above a respective normal threshold; and
a second level in response to a particular aspect of each of the characteristic data, physical examination data, and clinical diagnostic data, of the plurality of elements, being above a respective normal threshold.

22. The system of claim 21, wherein the operations further comprise:
comparing the first level and the second level; and based on the comparison selecting a highest of the first level and the second level as the risk rating for a patient.

23. The system of claim 1, wherein the operations further comprise initiating the treatment remedial action.

24. The system of claim 1, wherein the treatment remedial action is applied to a particular patient to bring hormone measurements associated with the particular patient into a normal range for the particular patient.

25. The system of claim 1, wherein the one or more hardware processors comprise a distributive adaptive agent that includes a neural network.

26. The system of claim 1, wherein the operations further comprise:
performing sequential modeling using one or more models that include multiple Rotterdam criteria to determine the risk level of PCOS,
wherein the one or more models include the predictive diagnosis electronic model.

27. The system of claim 1, wherein the first set of values representing the set of the patient information including the particular type of information comprises imaging data.

28. The system of claim 1, wherein applying the predictive diagnosis electronic model further comprises:
excluding data related to nonclassical congenital adrenal hyperplasia (NCCAH) from the patient information before applying the predictive diagnosis electronic model to the patient information.

29. The system of claim 1, wherein the operations further comprise updating the predictive diagnosis electronic model based on information corresponding to additional data selected from the group comprising characteristic information, physical examination information, clinical diagnostic information, and risk level information, and applying the updated predictive diagnosis electronic model to additional patient information.

30. The system of claim 1, wherein the predictive diagnosis electronic model is generated based at least in part on historical clinical data (i) corresponding to a plurality of patients and (ii) indicating PCOS risk information.

31. The computer implemented method of claim 8, wherein the first set of patient criteria indicates a non-adolescent patient, and wherein the first set of values representing the set of the patient information including the particular type of information corresponds to imaging data.

32. The system of claim 1, wherein the one or more decision elements comprise one or more decision trees.

33. The system of claim 32, wherein the predictive diagnosis electronic model is configured based on a plurality of decision trees and based at least partially on the characteristic information, the physical examination information, the clinical diagnostic information, and the risk level information.

34. The system of claim 1, wherein the predictive diagnosis electronic model comprises a predictive diagnosis model trained based on the characteristic information, the physical examination information, the clinical diagnostic information, and the risk level information.

35. The system of claim 34, wherein the predictive diagnosis electronic model is trained based on logistic regression.

36. The computer implemented method of claim 8, further comprising:
   after the configuring and prior to applying the predictive diagnosis electronic model to the patient information, accessing stored patient criteria associated with the predictive diagnosis electronic model.

37. The computer implemented method of claim 36, further comprising:
   in response to the accessing, comparing the stored patient criteria and the patient information;
   and changing the patient information input to the predictive diagnosis electronic model based the comparison.

* * * * *